(12) United States Patent
Roy et al.

(10) Patent No.: US 8,804,906 B2
(45) Date of Patent: Aug. 12, 2014

(54) TECHNIQUE TO ENHANCE THE CLINICAL EFFICIENCY OF RADIOTHERAPY AND RADIOSURGERY USING PERTURBATIVE BEAMING AND TISSUE-SPECIFIC RADIOBIOLOGY

(75) Inventors: Prasun Roy, Gurgaon (IN); Subhadip Paul, Gurgaon (IN)

(73) Assignees: Department of Biotechnology, New Delhi (IN); National Brain Research Centre, Haryana (IN)

( * ) Notice: Subject to any disclaimer, the term of this patent is extended or adjusted under 35 U.S.C. 154(b) by 665 days.

(21) Appl. No.: 13/133,023

(22) PCT Filed: Feb. 10, 2009

(86) PCT No.: PCT/IN2009/000094
§ 371 (c)(1),
(2), (4) Date: Dec. 9, 2011

(87) PCT Pub. No.: WO2010/052730
PCT Pub. Date: May 14, 2010

(65) Prior Publication Data
US 2012/0106703 A1    May 3, 2012

(30) Foreign Application Priority Data
Nov. 4, 2008 (IN) .............................. 2494/DEL/08

(51) Int. Cl.
*A61N 5/10* (2006.01)
(52) U.S. Cl.
CPC .................................... *A61N 5/1042* (2013.01)
USPC .......................................................... 378/65

(58) Field of Classification Search
CPC ....... A61N 5/10; A61N 5/1042; A61N 5/1048; A61N 5/1031
USPC ...................................... 378/64, 65, 108, 145
See application file for complete search history.

(56) References Cited

U.S. PATENT DOCUMENTS

| 7,835,492 B1 * | 11/2010 | Sahadevan ...................... 378/65 |
| 2005/0231138 A1 | 10/2005 | Nakanishi et al. |
| 2007/0286343 A1 | 12/2007 | Maciunas et al. |

OTHER PUBLICATIONS

Brenner D. et al., A convenient extension of the linear-quadratic model to include redistribution and reoxygenation, Int. J. Radiation Oncology Biol. Phys., 1995, pp. 379-390, vol. 32, No. 2.
Horsthemke W. and Lefever R., Noise-induced Transitions in Physics, Chemistry and Biology. 2d ed. 2006, pp. 235-239, Springer, Berlin.
Murphy GP et al., American Cancer Society Textbook of Clinical Oncology, 2000, p. 116, American Cancer Society, Atlanta.
Risken H., The Fokker-Planck Equation, 1982, pp. 50-54, New York.

(Continued)

*Primary Examiner* — Irakli Kiknadze
(74) *Attorney, Agent, or Firm* — The Webb Law Firm (57) ABSTRACT

This invention relates to a technique to enhance the clinical efficiency of radiotherapy and readiosurgery using perturbative beaming and tissue specific radiobiology, comprising, Considering the normal steady beam dose rate, then increasing the temporal stochastic fluctuation of the output intensity of the radiation beam from a medical linear accelerator or cobalt gamma knife beam setup, developing a computer-based methodology by considering the tumor specific radiobiology and magnitude of the tailor made dose rate fluctuation using an embedded system device consisting of requisite hardware and software as described herein.

5 Claims, 5 Drawing Sheets

(56) References Cited

OTHER PUBLICATIONS

Van Kampen NG, Stochastic Processes in Physics and Chemistry. 3d ed., 2007, pp. 55-58, North Holland.

Yang Y. and Xing L., Optimization of radiotherapy dose-time fractionation with consideration of tumor specific biology, Medical Physics, Dec. 2005, pp. 3666-3677, vol. 32, No. 12.

* cited by examiner

TECHNIQUE TO ENHANCE THE CLINICAL EFFICIENCY OF RADIOTHERAPY AND RADIOSURGERY USING PERTURBATIVE BEAMING AND TISSUE-SPECIFIC RADIOBIOLOGY

FIELD OF INVENTION

This invention relates to a novel method to enhance the efficacy of radiation therapy or radio surgery by increasing the malignant cell elimination without increasing the radiation dose.

BACKGROUND OF INVENTION

Radiation therapy is the most common modality of cancer treatment; across the world annually 50% of the cancer patients receive radiation administration. Generally beams of particles are used to treat malignant tissue, using photon (x-ray/γ-ray), or electron, which produce low linear-energy transfer to the tissue. These beams are generated usually by means of linear accelerators or radioactive sources. These types of radiotherapy or radiosurgery facilities are widely used in clinics and hospitals. However, the main problem is that, in conventional radiation therapy, it is difficult to eradicate the cancer cells successfully and tumour recurrence occur which causes therapeutic failure.

Generally beams of particles are used to treat malignant tissue in radiation therapy, most commonly photon (x-ray, γ-ray) or electron. These beams are generated using linear accelerators or radioactive elements. In conventional radiotherapy systems, each beamlet is steady from moment to moment and there is no arrangement of temporally perturbing or fluctuating the dose rate intensity of the beamlet momentarily with time (though intensity may differ among beams at different positions). In intensity-modulated radiotherapy, there may be inter-beamlet variation spatially (and not intra-beamlet variation temporally), and it is the latter intra-beamlet temporal fluctuation that is embodied in this invention. In existing accelerators, the beamlets from different angles are administered successively (unlike the simultaneous administration of all the beamlets together confocally on the tumour which is elucidated in this invention). In existing radioactive gamma-knife also, the intensity of the beamlets cannot be temporarily varied, however the proposed methodology incorporates their temporal fluctuation.

In existing radiotherapy protocols, the tumour cells are usually not eradicated and cancer recurrence generally ensues later. For instance, as mentioned earlier, an average 1 inch diameter tumour will still have, after the full standard conventional radiotherapy course, about 100 malignant cells (slow-growing tumours) or 10 malignant cells (fast-growing tumours), and it is these cells that multiply causing recurrence of the disease. Moreover, conventional dose schedule are arbitrary and not adapted to the radiobiological character of the tumour. Furthermore, normal tissue is also killed considerably, producing radiation toxicity, and in the brain there is toxic necrosis and gliosis, together with associated dementia and cognitive deterioration which is a serious side-effect of radiotherapy in neuro-oncology. Due to this reason one cannot use radiotherapy in brain tumours of very young children whose cognitive and mental development is ongoing.

Inventors develop three principles: fluctuative dosing, confocal beaming, and adapting to tumour tissue-specific radiobiological milieu. We synthesize the administration of these three approaches in an orchestrated symbiotic strategy. We tailor-make the treatment duration, the fluctuation level and the dose profiling, by adjusting the therapy to the tumour tissue itself. Thus the suggested technique ensures the selective killing of tumour cells and protecting the normal cells by using the following measures:

Confocal Beaming

Stochastic Perturbation that strikingly increases tumour cell kill but not appreciable normal cell kill Reducing the radiotherapy treatment duration required to fully eliminate tumour cells Diminishing the cumulative radiotherapy dose required for this elimination.

Decreasing total cumulative dose to decrease radiotoxicity and associated dementia.

Making radiotherapy a possible option in paediatric brain tumours, due to our reduceable cumulative dose.

The above strategies do indeed maximize the therapeutic differential of radiotherapy.

The principle of adding optimal stochastic fluctuation (gaussian perturbation) to a therapeutic signal, has been studied by researchers for numerous clinical applications to increase efficiency of various therapeutic modalities, such as in pulmonary ventilation, stroke, muscular rehabilitation, deafness and hypertension. The said principle is referred to variously as stochastic resonance, noise-induced transition or stochastic activation. Furthermore, stochastic fluctuation of photon beam has also been used to alter efficiency of photo-chemical/photobiological effects where chemical/biochemical reactions are actuated by photons (light). However, there has been no record of therapeutic use of stochastic fluctuation of photobiological effects, such as in photon-tissue interaction in radiotherapy using x-ray or γ-ray.

Stochastically-modulated radiotherapy beaming as proposed in the present methodology, has not been used earlier, and there is no literature available regarding the use of stochastic dose-rate fluctuation of beam to maximize the therapeutic effect in radiotherapy. However, there have been earlier endeavours for upgrading the efficiency of radiotherapy using conventional optimization procedures on standard deterministic (non-stochastic) radiotherapy. Nevertheless there is only moderate improvement at most, the tumour cells are generally not eradicated and recurrence duly ensues. Under these conditions, the oncology and therapeutic radiology community, and more so the neuro-oncological community, do really appreciate the crucial need of novel radiotherapetic interventions which can radically eliminate tumour cells (which can be done by the proposed methodology).

OBJECT OF INVENTION

The main object is to provide a method to enhance the efficacy of radiotherapy/radiosurgery by increasing the malignant cell killing without increasing the total dose.

Other object is to eliminate cancer cells successfully in order to prevent tumour recurrence.

Another object is to increase the therapeutic differential, and under specific conditions, decrease the total dose administered, thus diminishing the radiation toxicity in organs.

Yet another object is to decrease under particular conditions, the radiation-induced dementia, which is a most critical limitation in conventional radiotherapy of brain tumours.

Further object is to make suitable choice of the daily fraction delivery time (in minutes per day), as well as the total duration of the radiotherapy treatment schedule (in weeks), in order to maximize the therapeutic efficacy.

Other object is to adapt the treatment to biological characteristics of tumour tissue, namely tumor-specific radiobiology, so that the therapy is optimally effective for the tumour.

Another object is to provide a tailor to provide a tailor-made embedded system, whereby the proposed stochastic algorithm interfaces with the pulse programming hardware unit and cathode injector unit of a medical linear accelerator, whereby the accelerator administers the desired optimized stochastically-profiled beam.

STATEMENT OF INVENTION

This invention relates to a technique to enhance the clinical efficiency of radiotherapy and readiosurgery using perturbative beaming and tissue specific radiobiology, comprising, Considering the normal steady beam dose rate, Then increasing the amplitude of temporal stochastic fluctuation of the output intensity of the radiation beam from a medical linear accelerator or cobalt gamma knife beam setup, Developing a computer-based methodology by considering the tumor specific radiobiology and magnitude of the tailor made dose rate fluctuation using an embedded system device consisting of requisite hardware and software as described herein.

BRIEF DESCRIPTION OF THE ACCOMPANYING DRAWINGS

Schema 1 shows Flow sheet algorithm for determining the intensity of radiotherapy fluctuation so that the survival fraction of tumour cells falls to a predetermined very low value.

(a) Survival fraction plotted as radiotherapy progresses for 30 days. The sloping lines are for fluctuation $\sigma_f$=0% (conventional radiotherapy), 2.5%, 5%, and 7.5% (from top to bottom); the sloping graphs denotes the survival fractions of tumour cells. The small horizontal steps in these sloping lines denote that the tumor cells are not eliminated on the weekends as radiotherapy is not administered during weekend days. The long horizontal line (the tumour elimination threshold line) represents the value of survival fraction at which full elimination of tumour cells occur. In conventional radiotherapy, tumour cells are not fully eliminated during radiotherapy protocol as the survival fraction of the tumor cells at the end of the radiotherapy course is above the tumor elimination threshold. Note that the $\sigma_f$=5% curve crosses the threshold line at 30 days, implying full elimination of tumour cells (circle). Here, the daily dose is 2 Grays, and the daily fraction delivery time is 20 minutes, for all the sloping curves.

(b) Survival fraction after 30 days of radiotherapy at different values of fraction delivery time. From top to bottom: curves for fluctuation $\sigma_f$=0% (conventional), 2.5%, and 5%. Shorter fraction delivery times result more tumour cell killing. More tumour cells are killed if daily fraction delivery time is lower (i.e. if the dose-rate per minute is higher). Daily dose is 2 Grays.

FIG. 2 demonstrates Slowly proliferating tumour: Here also, stochastic fluctuation in the radiotherapy beam prominently decreases the survival fraction of malignant cells. We consider the radiotherapetic effect after a fortnight (16 days). The sloping curves in FIG. 2a have the same fluctuation values as FIG. 1a.

(a) Survival fraction plotted as radiotherapy progresses for 16 days: Observe that the 5% fluctuation curve crosses the threshold line at 16 days (circle), implying full elimination of tumour cells. From top to bottom: curves for fluctuation $\sigma_f$=0% (conventional), 2.5%, 5%, 7.5%. The long horizontal line (the tumour elimination threshold line) represents the value of survival fraction at which full elimination of tumour cells occur. Here, as before, the daily dose is 2 Grays, and the daily fraction delivery time is 20 minutes for all the sloping curves.

(b) Survival fraction after 16 days of radiotherapy at different values of fraction delivery time. From top to bottom: curves for fluctuation $\sigma_f$=0% (conventional), 2.5%, and 5%. Stochastic fluctuation in the radiotherapy beam decreases much more the survival fraction of malignant cells in slow-growing tumours when compared with fast growing tumours. Here also, more tumour cells are killed if daily fraction delivery time is lower (i.e. if the dose-rate per minute is higher). As in the earlier case, the daily dose is 2 Grays.

FIG. 3 shows Therapy evaluation and modeling system for stochastic radiotherapy: Representative templates. (a) Initial MRI scan of brain showing fast-growing glioma tumour, contrast-agent as gadolinium used. (b) Target tissue of the tumour for radio-therapy, the necrotic zone is shown by the central hypointense darker area, marked by low vascularization and low contrast media uptake, having considerably less density of tumour cells in necrotic zone. (c) Tumour cell density, shown by white spots, at end of $10^{th}$ day of stochastic radiotherapy. (d) Tumour cell density at end of $15^{th}$ day. (e) Same, at end of $18^{th}$ day. (f) Same, at $30^{th}$ day, the end of the protocol. Note full elimination of tumour cells in (f).

(a) Survival Fraction of Normal Tissue during stochastic radiotherapy of fast-growing tumour.

(b) Survival Fraction of Normal Tissue during stochastic radiotherapy of slow-growing tumour.

Note that the in both cases, the survival fraction of normal tissue is satisfactory, namely over 90%.

DETAILED DESCRIPTION OF THE INVENTION

The present invention provides a novel method to enhance the efficacy of radiation therapy or radio-surgery by increasing the malignant cell elimination without increasing the radiation dose. Enhancement of malignant cell kill is achieved by considering the normal steady beam dose rate, and then increasing the temporal stochastic fluctuation of the output intensity of the radiation beam from a medical linear accelerator or cobalt gamma knife beam set-up. A computer-based methodology is developed by considering the tumor specific radiobiology and magnitude of the tailor-made dose-rate fluctuation administered. This methodology enables a medical physicist or therapeutic radiologist to make a suitable optimal choice of radiotherapy protocol parameters.

Through a specific embedded system as proposed in this invention, the algorithm developed here interfaces with the pulse output unit of the linear accelerator or channel output unit of a cobalt gamma-knife, whereby one can administer the desired beam whose intensity is made to vary stochastically with a particular value of variance, i.e., a mean-zero gaussian perturbation is impressed on the steady beam dose rate. The proposed technique critically increases tumour-cell lysis, without increasing radiation. The procedure may also be used to increase the therapeutic differential, and decrease the total dose administered, thus appreciably decreasing the radiation toxicity. The technique is implemented using an Embedded System device consisting of requisite hardware and software, the elements of the Embedded System instrumentation and its operation of the linear accelerator are delineated later.

In prevalent radiation therapy treatment, stochastic modulation of dose-rate is not used, only steady deterministic beam is administered. In this invention we provide a novel method of radiotherapy that uses the concept of stochastic activation or stochastic resonance, whereby one can use stochastic fluctuation of an input signal to increase the target effect of the signal (here the signal is the photon radiotherapy beam, while the target effect is cytolysis of tumour tissue). In order to enhance the therapeutic efficacy of radiation therapy, the proposed methodology also enables one to suitably optimize the following parameters of radiotherapy:

Daily exposure fraction delivery time (in minutes)
Dose rate (in watts, or grays/minute)
Total duration of treatment (in weeks)
Total dose administered across the full duration of treatment (in grays or joules).

Conventional radiotherapy protocols cannot eliminate all the cancer cells selectively from the normal cells; however the suggested procedure, using confocal beaming, tends to increase this selectivity by increasing the tumour cell lysis while normal cell lysis is not increased. The procedure is tailored to tumor specific radiobiology, whereby the radiobiological profile of tumour tissue is utilized to maximally optimize the therapeutic output quantitatively. Thus, this invention provides an advanced method of radiation treatment to cancer patients.

This invention provides a novel technique to increase radiotherapy-induced tumour cell kill without increasing radiation dose. The utility of the present invention is to provide the methodology to increase the therapeutic efficacy of the radiotherapy/radiosurgery system by administering a stochastic mean-zero dose-rate fluctuation waveform onto the beam of a medical linear accelerator or cobalt gamma knife beam set-up. The methodology also enables one to make a suitable optimal choice of the radiotherapy protocol. The procedure is also biologically adapted or tailored to tumor-specific radiobiology, and utilizes the radiobiological profile of the tumour tissue to maximally optimize the therapeutic output quantitatively.

(a) Quantification of Cell Survival:

If dose D (in Grays) is administered during the radiation exposure time t of an exposure (fraction), then, according to linear-quadratic radiobiological (LCR) scheme[1], one has the following equation denoting the survival fraction S of the cells, that is, the fraction of cells surviving after the dose D of radiation:

$$S = S_0 \exp\left[\begin{array}{l} -\{\alpha D\} - \{\beta G(\tau_R)D^2\} + \\ \{\left(\frac{1}{2}\sigma^2\right)G(\tau_S)D^2\} + \{H(t, T_k) \times t/T_{pd}\} \end{array}\right] \quad [1]$$

where $S_0$ is the original fraction of cells in the tissue which are malignant (the rest are normal). The first term in braces { } represents cell killing by one-track action (single strand DNA break), the second term in braces describes killing by two-track action (double strand DNA break) with possible repair, the third braced term refers to intercellular diversity of radiosensitivity and resensitization (redistribution, reoxygenation), while the fourth braced term stand for delayed accelerated repopulation. Here, $\alpha$ and $\beta$ are the first and second order radiation sensitivity parameters of the cells, $G(\tau)$ is the generalized Lea-Catcheside function, H the Heaviside step function occurring at time $T_k$ (the Kick-off time of the cells for accelerated repopulation), $\sigma$ is the standard deviation of the Gaussian distribution of $\alpha$ parameter in the subpopulations of cells, while $\tau_R$, $\tau_S$ and $T_{pd}$ are respectively the Repair half-time, the average (re)Sensitization time, the Potential Doubling time, with regard to the tumour cells. The Lea-Catcheside function $G(\tau)$ is:

$$G(\tau) = 2\left(\frac{\tau}{t}\right)^2\left[\exp\left(-\frac{t}{\tau}\right) - 1\right] + \frac{2\tau}{t}$$

Now let $I_0$, expressed in Grays/sec, denote the dose-rate of the deterministic level of radiation, and t is the time duration of continuous radiation exposure, that is, $D=I_0 t$. Now substituting these expressions in equation [1], we get the formulation of survival fraction of tumour cells in the realistic radiobiological tissue environment, under a deterministic steady radiotherapy beam:

$$S_t = S_0 \exp\left[-\alpha I_0 t + I_0^2\left\{\frac{\sigma^2\tau_S^2\exp\left(-\frac{t}{\tau_S}\right) - 2\beta\tau_R^2\exp\left(-\frac{t}{\tau_R}\right) +}{(\sigma^2\tau_S - 2\beta\tau_R)t + (2\beta\tau_R^2 - \sigma^2\tau_S^2)}\right\} + H(t, T_k) \times t/T_{pd}\right] \quad [2]$$

Then, utilizing the techniques of stochastic operations and nonlinear dynamics[2-4], we have obtained the expected survival fraction of cells under the condition of stochastically fluctuating beam:

$$S_S = S_0 \exp\left[-\alpha I_0 t + I_0^2\left\{\frac{\sigma^2\tau_S^2\exp\left(-\frac{t}{\tau_S}\right) - 2\beta\tau_R^2\exp\left(-\frac{t}{\tau_R}\right) +}{(\sigma^2\tau_S - 2\beta\tau_R)t + (2\beta\tau_R^2 - \sigma^2\tau_S^2)}\right\} + H(t, T_k) \times t/T_{pd} + f_{LQR}(\sigma_f)\right] \quad [3]$$

where the last term $f_{LQR}$, is the extra effect on the survival fraction due to the stochastic fluctuation in the dose rate. The term $f_{LQR}$ is given by:

$$f(\sigma_f) = \frac{\sigma_f^2}{2}\left[\alpha^2 t + (1 - 4\alpha I_0)X + \left(4I_0 + \frac{\sigma_f^2}{2}\right)Y\right] \quad [4]$$

where the symbols X and Y have the following expressions:

$$X = \left\{\begin{array}{l} \sigma^2\tau_S^2\exp\left(-\frac{t}{\tau_S}\right) - 2\beta\tau_R^2\exp\left(-\frac{t}{\tau_R}\right) + \\ (\sigma^2\tau_S - 2\beta\tau_R)t + (2\beta\tau_R^2 - \sigma^2\tau_S^2) \end{array}\right\} \quad [5]$$

$$Y = \left[\begin{array}{l} \frac{\sigma^4\tau_S^2}{2}\left\{1 - \exp\left(-\frac{2t}{\tau_S}\right)\right\} + 2\beta^2\tau_R^3\left\{1 - \exp\left(-\frac{2t}{\tau_R}\right)\right\} + \\ \frac{4\beta\sigma^2\tau_R\tau_S}{(1/\tau_R + 1/\tau_S)}\left\{\exp\left(-t\left(\frac{1}{\tau_R} + \frac{1}{\tau_S}\right)\right) - 1\right\} + Z \end{array}\right] \quad [6]$$

In eq. [6], the last term Z is determined as:

$$Z = (\sigma^2 \tau_S - 2\beta\tau_R) \quad [7]$$
$$\left\{ 4\beta\tau_R^2\left(1 - \exp\left(-\frac{t}{\tau_R}\right)\right) + 2\sigma^2\tau_S^2\left(1 - \exp\left(-\frac{t}{\tau_S}\right)\right) + (\sigma^2\tau_S - 2\beta\tau_R)t \right\}$$

The extra stochastic effect on the cell kill, namely $f_{LQR}$ in eq. (3), is numerically negative in the clinically used dose range; thus the effect reduces the survival fraction, indicating more efficient cell killing. As worked out by us, this scheme is the "LQRF" (LQR+Fluctuation) format of cell survival under stochastically fluctuating radiotherapy, and the equation has been subsequently re-confirmed by us using biologically-based boundary conditions. In our study, the effect of stochastic temporal dose-rate fluctuation on cell survival was realized by adding mean-zero Gaussian fluctuation at the white noise limit. The fluctuation or noise intensity is varied up to 10% of the dose-rate. As the mean value of the fluctuation is zero, the dose amount does not increase.

It may be mentioned that in a tumour of 1 inch diameter, there are $10^{10}$ tumour cells[5]. Thus for eliminating tumour cells fully, the survival fraction for a desirable therapy should fall below $10^{-10}$ so that the last malignant cell is eliminated. One may note that as per standard clinical radiotherapy protocol, viz. 2 Grays/day exposure for 35 working days (i.e. 47 days including weekend gaps)[5], the survival fraction is about $9.7 \times 10^{-10}$ and $1.1 \times 10^{-7}$ for fast and slow growing tumours respectively, implying that there will still be around 10 and 100 malignant cells correspondingly, after radiotherapy treatment. It is these malignant cells that produce tumour recurrence later. Increasing the radiotherapy dose to lyse all the tumour cells is not possible as the relationship of cell kill with dose under eq. [2] reaches a plateau.

(c) Choice of dose parameters: Daily fraction delivery time (minutes), Total duration of treatment (weeks), and Total dose across treatment duration (in grays or joules):

It has been mentioned that the quantitative procedure and computational oncology algorithms for determination of the dose parameters has been developed and the technique has been tested on a customized therapy evaluation system that is based on using models of several kinds of malignant lesions incorporating both rapidly-growing tumours (as glioblastoma or fibrosarcoma) and slowly-growing tumours (as meningioma or adenocarcinoma) which are used as therapy testing/planning targets. The effect of our dose-rate fluctuation scheme on standard fractionated radiation therapy protocol was realized using a computational radiotherapy design and evaluation system, both in the case of fast and slowly proliferating tumors. The following examples are given by way of explanation and for illustration only and these examples should not be construed in any manner to limit the scope of invention.

Survival fractions were computed via eq. [3] above, using radiobiological parameters specific to the slow and fast growing tumours, as the case may be (namely the radiobiological parameters $\alpha$, $\beta$, $\sigma$ $T_k$ etc)[6]. As per convention, this radiotherapy dose is not administered every sixth and seventh days which are weekends. The Survival fraction as the treatment progresses across the weeks was calculated for different durations of the daily fraction delivery time t, and for different magnitudes of dose-rate fluctuation $\sigma_f$, by means of the algorithm given as a flow chart in Schema-I.

The following user specified input parameters provide the details of fractionation radiotherapy protocol:
t=daily fraction delivery time in minutes
Δt=change in daily fraction delivery time in minutes
D=daily dose in Grays (2 Grays as per standard protocol),
$I_0$=dose rate during exposure (note, $I_0$=D/t)
$t_{LOW}$=minimum duration of the daily fraction delivery time (this is 5 minutes and is limited by the startup inertia of the accelerator hardware),
i corresponds each day in radiotherapy protocol
$i_{Final}$=total duration of protocol, in number of days
$S_{Fix}$=minimum survival fraction which is desired to achieve at the end of the therapy protocol
$S_{LQRF}$=survival fraction achieved due to stochastic perturbation of beam
$\sigma_f$=amplitude of the Fluctuation in dose-rate
$\sigma_F$=maximum limit of amplitude of the Fluctuation in dose-rate (a value of $\sigma_F$ is 20% of the dose rate $I_0$, can be readily implemented by readily available hardware).

In the following examples the daily exposure time t is varied as in the clinical practice, i.e. 5 to 30 minutes, and $S_{Fix}=10^{-10}$. as mentioned earlier. Our objective is to see the change on the cell survival, if one alters the following variables: the fluctuation intensity $\sigma_f$, and the dose rate $I_0$ (or reciprocally the daily exposure time t).

References:
1. D. Brenner, L. Hlatky, P. Hahnfeldt, E. Hall, R. Sachs (2005), A convenient extension of the linear-quadratic model to include cell redistribution and reoxygenation, *International Journal of Radiation Oncology, Biology and Physics*, 32, 379 (1995).
2. N. G. van Kampen, *Stochastic Processes in Physics and Chemistry*, 3$^{rd}$ ed, North Holland, 2007.
3. W. Horsthemke, R. Lefever, Noise-induced Transitions in Physics, Chemistry and Biology, 2$^{nd}$ ed, Springer, Berlin, 2006.
4. H. Risken, The Fokker-Planck Equation, New York, 1982.
5. G. P. Murphy, W. Lawrence, R. E. Lenard, *American Cancer Society Textbook of Clinical Oncology*, American Cancer Society, Atlanta, 2000
6. Y Yang, Lei Xing, Optimization of radiotherapy dose-time fractionation with consideration of tumor specific biology, *Medical Physics*, 32, 12 (2005).

Figure 1:
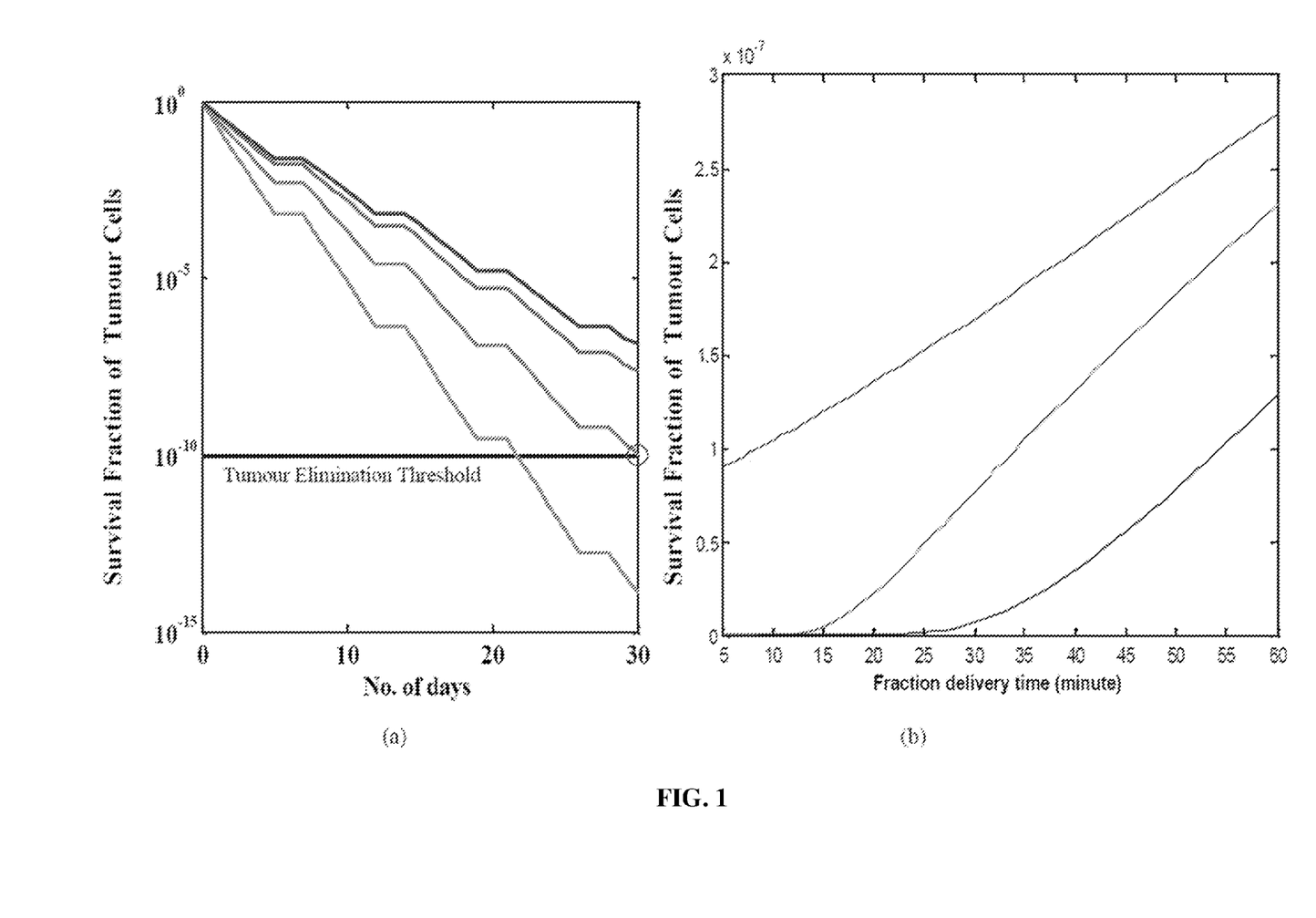
FIG. 1 illustrates Fast-proliferating tumour: Stochastic fluctuation in the radiotherapy beam strikingly decreases the survival fraction of malignant cells, when compared to conventional beaming (deterministic).

Illustrative Examples (i) Fast Proliferating Tumour:

It is known that the radiobiological parameters for representative fast proliferating tumour are $\alpha=0.35$/Gy, $\beta=0.035$/Gy$^2$, $\tau_R=0.5$ hour, $\tau_S=1$ day, $\sigma=0.2$, $T_k=4$ weeks (28 days), $T_{pd}=3$ days[6]. The daily dose D was 2 Gray, and the daily beam exposure duration t was taken to be 20 minutes as per conventionally used protocols; hence the dose rate $I_0$ is 0.2 Grays/minute. In our study, the dose-rate fluctuation $\sigma_F$ was increased till 7.5% of the dose-rate. Using the methodology of eq. [3] and the algorithm outlined in the given flow chart (Schema-I), we find that a perturbation of 5%, a treatment duration of 30 days is needed to fully eliminate the tumour cells. FIG. 1(a) gives the survival fraction of tumour cell after 1 month (30 days) of radiotherapy, under different values of the fluctuation %, the blue line shows the threshold survival fraction below which the tumour cells are fully eliminated.

In FIG. 1(a), note that the tumour cells are not eliminated under conventional deterministic radiotherapy ($\sigma=0$%), nor under lower fluctuation level as 2.5%. FIG. 1(b) gives the survival fraction after 1 month of radiotherapy, as the daily exposure time (or the daily dose-rate) is varied. Of course, the same daily dose of 2 Gray is given, but spread over an exposure duration ranging from 5 minutes to 60 minutes, corresponding to dose-rates of 0.4 Gray/minute to 0.033 Grays/minute. Here one may observe that the survival fraction of fluctuating radiotherapy is considerably lower, when compared to conventional (i.e. deterministic) radiotherapy.

Figure 2:
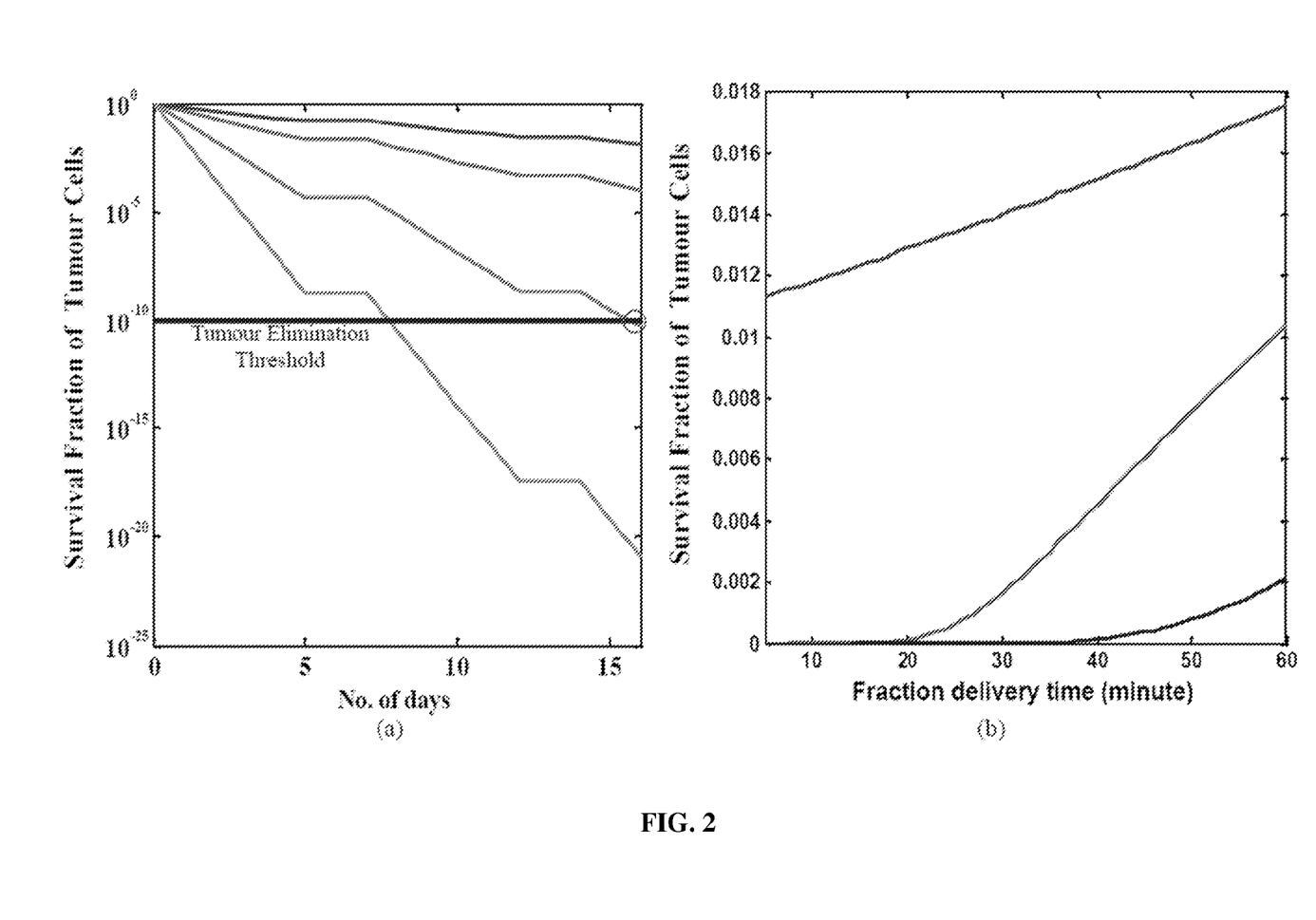

(ii) Slowly Proliferating Tumour:

The radiobiological parameters for representative slow proliferating tumour are known to be $\alpha=0.10/Gy$, $\beta=0.0666/Gy^2$, $\tau_R=1.9$ h, $\tau_S=2$ day, $\sigma=\sqrt{2\beta/3}$, $T_k=300$ days, $T_{pd}=40$ days[6]. Here also, the daily dose D was 2 Gray, and the daily beam exposure duration t was taken to be 20 minutes as per conventionally used protocols; hence the dose rate $I_0$ is 0.2 Grays/minute. Using the procedure of eq. [3] and the algorithm outlined in the given flow chart (Schema-I), we find the therapy duration when the tumour cells are eliminated completely at fluctuation of 5%. We find that this occurs after a fortnight, namely after 16 days [FIG. 2(a)]. One can clearly see the benefit of administering fluctuations to lyse tumour cells. FIG. 2(b) gives the survival fraction after 16 days radiotherapy, as the daily fraction delivery time, or dose-rate, is varied. Note that the cell kill of slowly-proliferating tumour in the conventional protocol is less than the fast growing tumour (survival fraction is higher), this is because the faster growing tumours are more radiosensitive than slow growing ones (the major radiosensitivity parameter $\alpha$ of fast growing tumours is about 3.5 times that of slow growing ones). However, the change due to the stochastic fluctuation is much more radical in slow-growing tumours, here the malignant cells are eliminated in about half the time required for elimination in fast-growing tumours (16 days versus 30 days at 5% fluctuation).

Therapy Evaluation, Confocal Delivery and Normal Tissue Preservation

Figure 3:
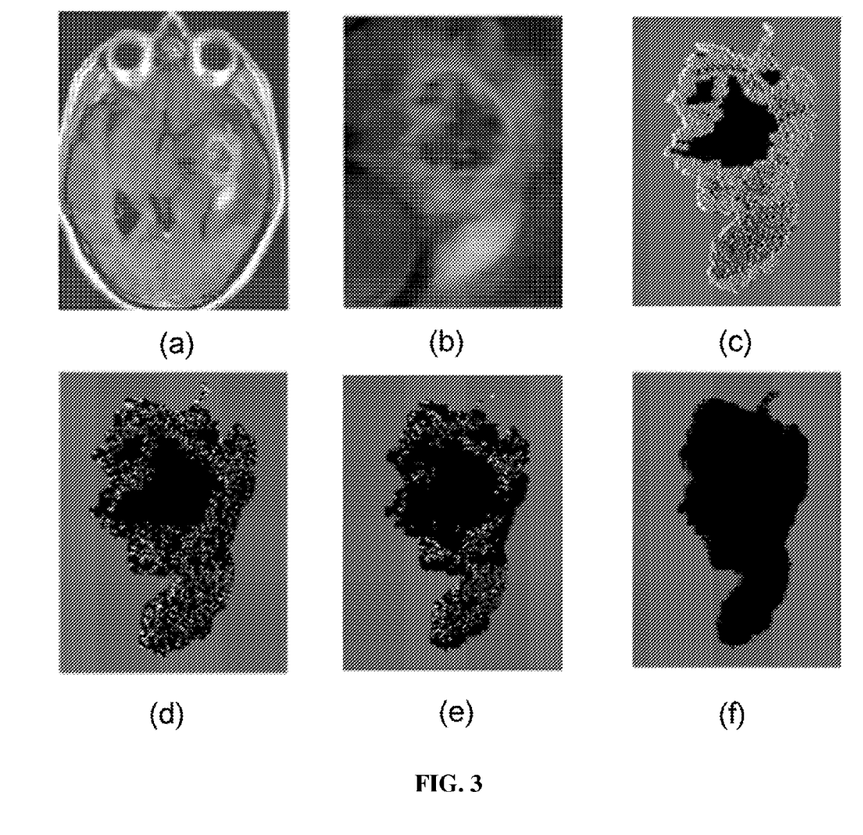

The effect of stochastic radiotherapy on tumour cell survival fraction as elucidated in eq. [3], has been evaluated on a customized therapy evaluation and planning system, whereby the testing has been done using models of several kinds of malignant lesions incorporating both fast- and slow-proliferating tumours having the representative radiobiological parameters (FIG. 3). We consider a linac with beam dose rate $I_0$, with a fluctuation level a of p % of the dose rate, i.e $\sigma=(p/100)\ I_0$. For actual implementation on an accelerator system, we put forward the use of a multiple beam linac using multi-beam distributors or beam splitters, which distributes the linac output beam into N beamlets that can be delivered simultaneously from N different angles. Thus the dose-rate $I_0$ of the linac divides off into the N beamlets each of dose-rate $I_0/N$. The N beamlets focus or intersect only across the tumour, and do not intersect in the normal tissue outside the tumour. The tumour tissue, where all the N beamlets intersect confocally has dose rate $I_0$. Since the main beam issues from the single electron gun of the accelerator, the fluctuations of all the beamlets are synchronous and hence constructively superpose in the tumour. Thus the fluctuation of each beamlet is p % of the dose rate of the beamlet, i.e. $(p/100)\ (I_0./N)$. When all the N beams converge on the tumour, the dose-rate in the tumour is $I_0$, while the fluctuation in the tumour is $(p/100)I_0$.

Figure 4:
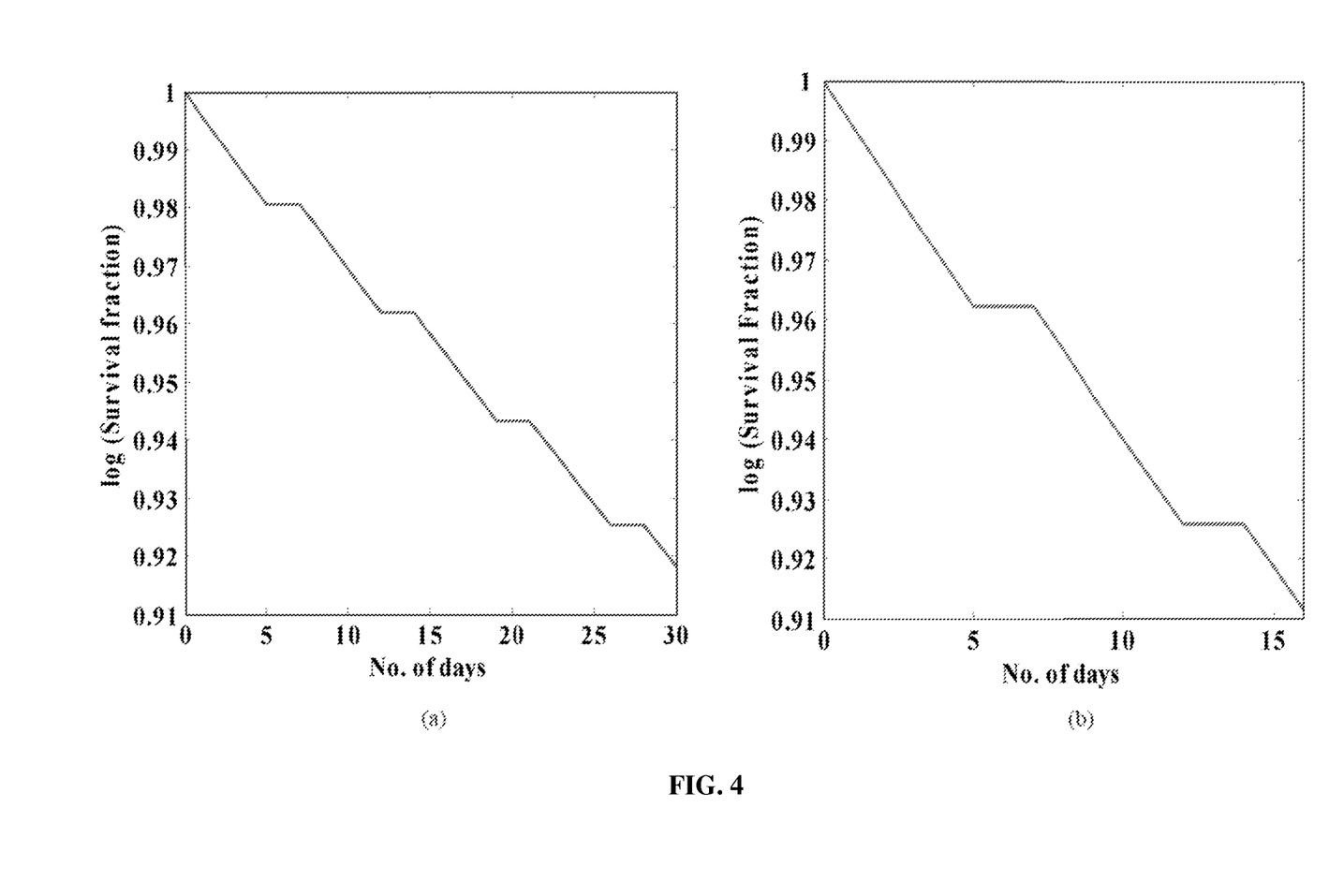
FIG. 4. Survival Fraction of Normal Tissue (SENT) under stochastic radiotherapy with 5% fluctuation level, confocal beamlets being used. Here, as in the earlier cases, the daily dose is 2 Grays, and the daily fraction delivery time is 20 minutes.

Any normal tissue outside the tumour will be traversed at most by only 1 beamlet of dose rate $I_0/N$, with fluctuation of $(p/100)\ (I_0./N)$. Using these reduced power and fluctuation incident in the normal tissue, we use the radiobiology evaluation system to find out the normal tissue kill, using the values of $\alpha$, $\beta$, and other radiobiological parameters for normal tissue. We test the formulation using 40-50 beamlets, which confocally converge on the tumour from various angles (radiobiological parameters of normal tissue[1]: $\alpha=0.35/Gy$, $\beta=0.035/Gy^2$, $\tau_R=0.5$ hour, $\tau_S=1$ day, $\sigma=0.2$, $T_k=4$ weeks (28 days), $T_{pd}=3$ days). We find that for fast-growing tumour, the survival fraction of normal tissue remains satisfactorily high (survival fraction=92%), at the end of our 30-day radiotherapy period, if one uses 50 beamlets (FIG. 4a). Correspondingly, we find that for slow-growing tumour at the end of our 16-day therapy period, the normal tissue survival is similarly high (91%), if one uses 40 beamlets (FIG. 4b).

Alternatively, instead of the multiple-beam linac set-up that delivers N beamlets, we can also use N small portable Linac tubes (Minac-type) placed at the N angles, their beams are fluctuated synchronously by the single Fluctuation programmer element using Matlab. The stochastic radiotherapy methodology can also be applied to radioactive units using cobalt (as gamma-knife equipment). Here, we can fill each beamlet channel tube with radio-opaque xenon gas (or other radio-opaque gases) whose pressure can be stochastically varied by connecting a side-tube from each beamlet channel tube to a common stochastic pump containing the gas. Stochastic variation of gaseous pressure produces similar variation in the gas density and its attenuation of gamma ray, and thus stochastically vary the intensity of the beamlet issuing out of each channel.

Figure 5:
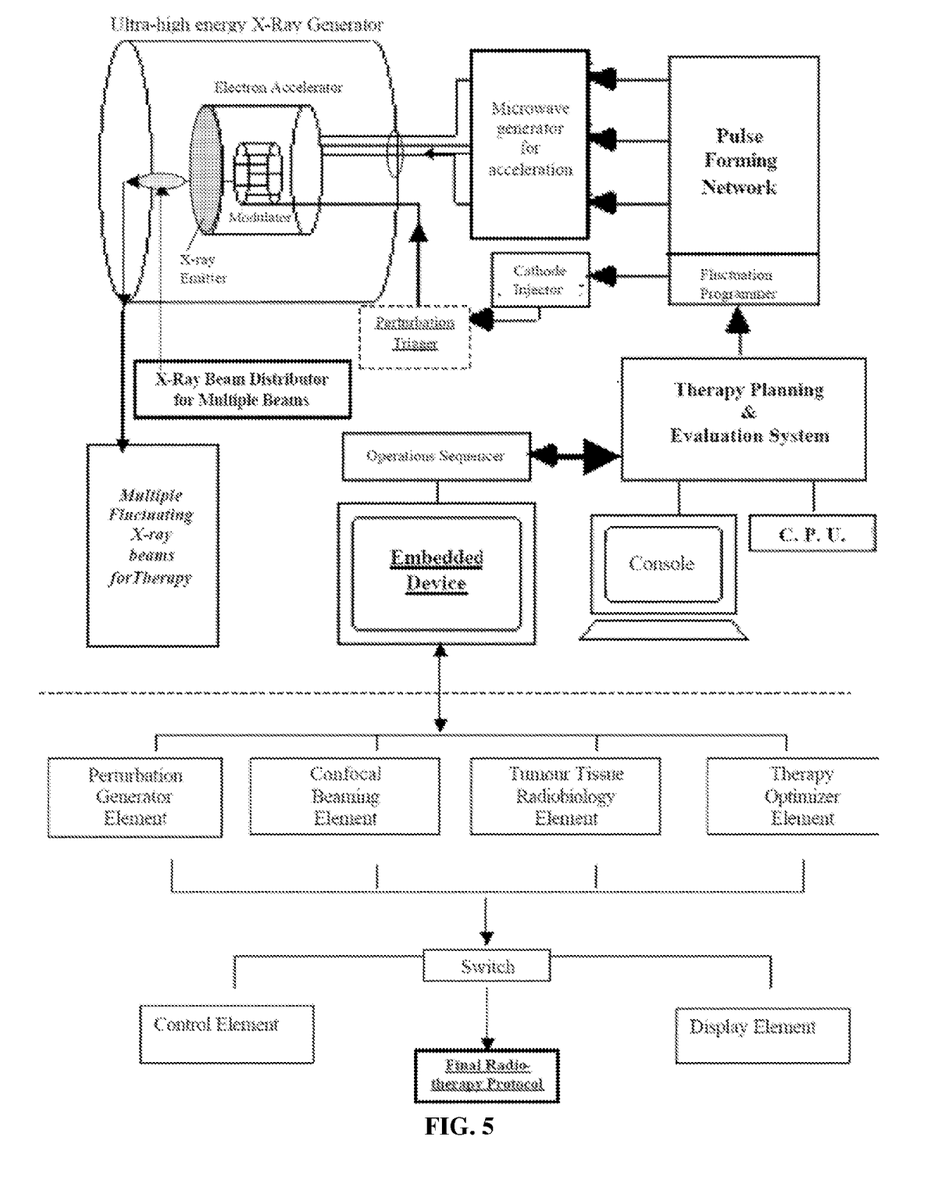
FIG. 5. demonstrates Constituents of the Embedded Device for the Perturbative Radiotherapy Instrumentation. The individual elements of the embedded system device are delineated below the horizontal dashed line.

Inventors now present a general design of the stochastic radiotherapy instrumentation. We first consider the case of linear accelerator radiotherapy whose beam output is $I_0$. Using an Embedded System device, consisting of requisite hardware and software, we design the fluctuation profile using a Fluctuation Programmer element, and this fluctuation profile is then forwarded towards the Cathode Injector of the electron gun, by means of a Perturbation Trigger. The trigger operates on the cathodic Modulator, thus stochastically fluctuating the intensity of the electron beam. The elements of our Embedded System device and its operation of the linear accelerator with beam distributor and distributed beamlets is schematically shown in FIG. 5. In case one uses N small linac tubes instead of beam distributor, then there are N linear accelerator tubes in parallel, each operated at dose-rate $I_0/N$ and fluctuation level at $(p/100)\ (I_0/N)$, while the Modulators of all the N tubes are synchronously controlled by a single Fluctuation Programmer. Secondly, if one considers therapy using radioactive source (e.g. cobalt gamma-knife), then the beamlet fluctuation can be induced by radio-opaque gas under pressure, actuated by a stochastic pump, as already mentioned.

Decrease in Radiotherapy Dosing: Normal Tissue Preservation to Prevent Radiation-Induced Dementia and Neurodegeneration At the daily dose fraction of 2 gray/working day, the total dose administered in fast growing tumours in our protocol of 30 days (comprising of 22 working days and 8 weekend days) are 44 Grays. Likewise the total dose for slow-growing tumour in our protocol (16 days, consisting of 12 working days) is 24 Grays. These doses are much lower than the 70 grays administered in conventional protocols of 47 days. Thus, if stochastic radiotherapy is used, we can avoid giving the full standard dose of 70 gray, and give the much reduced required doses of 44 Grays (or 24 Grays) which will enable the tumour cells to be completely eliminated. This reduction in total dose is important for reduction of radiotoxicity and toxic necrosis of tissue due to radiotherapy. It may be mentioned that in brain tumours, it is much desirable to reduce the total dose so that there is less incidence of dementia[5], which is a main side-effect or drawback of conventional radiotherapy at 70 Grays.

We claim:

1. A method to enhance the clinical efficiency of radiotherapy and radiosurgery using perturbative beaming and tissue specific radiobiology, comprising:

a) considering the normal steady beam dose rate, b) then increasing the temporal stochastic fluctuation of the output intensity of the radiation beam from a medical linear accelerator or cobalt gamma knife beam setup, and
c) developing a computer-based methodology by considering the tumor specific radiobiology and magnitude of the tailor made dose rate fluctuation using an embedded system device consisting of requisite hardware and software as described herein.

2. The method as claimed in claim 1, wherein through a specific embedded system, the algorithm developed interfaces with the pulse output unit of the linear accelerator or channel output unit of a cobalt gamma knife.

3. The method as claimed in claim 1, wherein the desired beam's intensity is made to very stochastically with a particular value of variance of a mean-zero Gaussian perturbation of the steady beam dose rate.

4. The method as claimed in claim 1, wherein it critically increases tumour cell lysis without appreciably increasing normal tissue lysis.

5. The method as claimed in claim 1, wherein the total dose administered to the tissue is decreased in comparison conventional radiotherapeutic protocols.

* * * * *

UNITED STATES PATENT AND TRADEMARK OFFICE
CERTIFICATE OF CORRECTION

PATENT NO. : 8,804,906 B2
APPLICATION NO. : 13/133023
DATED : August 12, 2014
INVENTOR(S) : Prasun Roy et al.

It is certified that error appears in the above-identified patent and that said Letters Patent is hereby corrected as shown below:

Title page of the Patent, Column 2, Item (57) Abstract, Line 2, delete "readiosurgery" and insert
-- radiosurgery --

Title page of the Patent, Column 2, Item (57) Abstract, Line 4, delete "Considering" and insert
-- considering --

Signed and Sealed this
Sixteenth Day of December, 2014

Michelle K. Lee
*Deputy Director of the United States Patent and Trademark Office*